(12) United States Patent
Chen et al.

(10) Patent No.: US 9,566,451 B2
(45) Date of Patent: Feb. 14, 2017

(54) METHOD AND DEVICE FOR IRRADIATION TREATMENT PLANNING

(75) Inventors: Wenjing Chen, Erlangen (DE); Alexander Gemmel, Erlangen (DE); Eike Rietzel, Weiterstadt (DE)

(73) Assignee: Siemens Aktiengesellschaft, München (DE)

( * ) Notice: Subject to any disclaimer, the term of this patent is extended or adjusted under 35 U.S.C. 154(b) by 259 days.

(21) Appl. No.: 13/446,875

(22) Filed: Apr. 13, 2012

(65) Prior Publication Data

US 2012/0264996 A1     Oct. 18, 2012

(30) Foreign Application Priority Data

Apr. 15, 2011 (DE) .......... 10 2011 007 498
May 31, 2011 (DE) .......... 10 2011 076 771

(51) Int. Cl.
*A61N 5/00* (2006.01)
*A61N 5/10* (2006.01)

(52) U.S. Cl.
CPC ........... *A61N 5/103* (2013.01); *A61N 5/1037* (2013.01); *A61N 5/1039* (2013.01)

(58) Field of Classification Search
CPC ............... A61N 5/103; A61N 5/1038; A61N 2005/1041; A61B 19/50
USPC .......... 13/1–9; 378/65, 4; 707/780; 600/407, 600/411, 417, 425, 427, 429; 382/294
See application file for complete search history.

(56) References Cited

U.S. PATENT DOCUMENTS

| | | |
|---|---|---|
| 6,411,675 B1 | 6/2002 | Llacer |
| 7,801,349 B2 | 9/2010 | Wang et al. |
| 2005/0201516 A1 | 9/2005 | Ruchala et al. |
| 2007/0100224 A1* | 5/2007 | Bova et al. ............. 600/407 |
| 2007/0286342 A1 | 12/2007 | Fuller |
| 2008/0037843 A1* | 2/2008 | Fu et al. ............. 382/128 |
| 2010/0056908 A1 | 3/2010 | Giller et al. |

(Continued)

FOREIGN PATENT DOCUMENTS

| | | |
|---|---|---|
| DE | 10 2008 044 901 A1 | 3/2010 |
| WO | WO 2010/018476 A2 | 2/2010 |

OTHER PUBLICATIONS

German Office Action dated Dec. 15, 2011 for corresponding German Patent Application No. DE 10 2011 076 771.1 with English translation.

(Continued)

*Primary Examiner* — Catherine B Kuhlman
(74) *Attorney, Agent, or Firm* — Lempia Summerfield Katz LLC

(57) ABSTRACT

A method for irradiation treatment planning for a target volume to be irradiated includes specifying a plurality of data sets. The target volume to be irradiated is depicted in each data set of the plurality of data sets. The data sets differ in that the target volume has another position and/or shape. A data set is selected from the plurality of the data sets and other data sets are registered to the selected data set. The method includes forming an amalgamation of the depicted target volumes using the registrations of the other data sets to the selected data set, and determining an area at risk in the selected data set. The method includes modifying the amalgamation of the target volumes such that the area at risk is excluded from the amalgamation of the depicted target volumes. An irradiation treatment plan is calculated using the modified amalgamation of the target volumes.

20 Claims, 5 Drawing Sheets

(56) References Cited

U.S. PATENT DOCUMENTS

2010/0088339 A1    4/2010  Rietzel et al.
2010/0232572 A1*   9/2010  Nord et al. ................. 378/65
2011/0103551 A1*   5/2011  Bal et al. .................... 378/65

OTHER PUBLICATIONS

European Search Report and Written Opinion dated Jun. 18, 2012 for EP 12 15 5721.9-2305 with English translation.
Y. Lei et al., "A Hybrid Strategy of Offline Adaptive Planning and Online Image Guidance for Prostate Cancer Radiotherapy," Physics in Medicine and Biology 55, pp. 2221-2234, 2010.
A. Buchali et al., "Impact of the Filling Status of the Bladder and Rectum on Their Integral Dose Distribution and the Movement of the Uterus in the Treatment Planning of Gynecological Cancer," Radiotherapy and Oncology 52, pp. 29-34, 1999.
ICRU Report 62, "Prescribing, Recording and Reporting Photon Beam Therapy (Supplement to ICRU Report 50)," Issued: Nov. 1, 1999, pp. 1-5.
B.S. Teh, et al., "Intensity-Modulated Radiation Therapy (IMRT) for Prostate Cancer with the Use of a Rectal Balloon for Prostate Immobilization: Acute Toxicity and Dose-Volume Analysis," Abstract, Int. J. Radiat. Oncol. Biol Phys., pp. 705-712, Mar. 1, 2001.
P. Keall, "4-Dimensional Computed Tomography Imaging and Treatment Planning," Seminars in Radiation Oncology, vol. 14, No. 1, pp. 81-90, Jan. 2004.

* cited by examiner

METHOD AND DEVICE FOR IRRADIATION TREATMENT PLANNING

This application claims the benefit of DE 10 2011 007 498.8, filed on Apr. 15, 2011. This application also claims the benefit of DE 10 2011 076 771.1, filed on May 31, 2011.

BACKGROUND

The present embodiments relate to a method and a device for irradiation treatment planning.

Prior to radiotherapy, an irradiation treatment plan is determined. This determination is sometimes difficult, since the internal anatomy of a patient may change over time. For example, target volumes inside the abdomen may change location from day to day or over the course of several days or weeks. A typical organ that is often subject to a change of position is the prostate. For example, the bladder, situated next to the prostate, and the rectum, situated next to the prostate, may exert an influence on the position and shape of the prostate depending upon the degree of filling of the bladder and/or the rectum.

One possibility of taking account of these changes is the use of safety margins. During irradiation treatment planning, safety margins are selected such that an internal displacement/deformation of the target volume is taken into account. Although the safety margins may moderate the adverse effects of a change of position of the target volume, the safety margins may lead to irradiation of adjacent, critical structures, such as the bladder or the rectum, for example.

A concept is known from US 2005/0201516 A1, with which a plurality of irradiation treatment plans with different safety margins (multiple-margin optimization with daily selection (MMODS)) may be calculated for a target volume. A user may choose in real time from a plurality of optimized irradiation treatment plans with different safety margins in order to take account of an observed change in the size or position of the tumor or the structures surrounding the tumor.

US 2010/0088339 A1 discloses a method, with which the most suitable irradiation treatment plan is selected from a plurality of previously established irradiation treatment plans prior to an irradiation fraction.

SUMMARY AND DESCRIPTION

The present embodiments may obviate one or more of the drawbacks or limitations in the related art. For example, a method or a device for irradiation treatment planning that calculates an irradiation treatment plan taking into account the possible changes to a location or a shape of a target volume is provided.

A method for irradiation treatment planning for a target volume to be irradiated involves the performance of the following acts.

A plurality of data sets is specified. The target volume to be irradiated is depicted in each data set of the plurality of data sets. The data sets differ in that the target volumes have different positions and/or shapes. For example, the data sets may be 3D imaging data sets such as, for example, computed tomography scans.

One data set is selected from the plurality of data sets. The other data sets of the plurality of data sets are registered to the one selected data set. The registrations (e.g., rigid, linear or affine registrations) are used to compare the data sets with respect to position and/or scaling. The registrations may be such that the transformed target volumes are not completely transformed to each other so that the transformed target volumes would then be congruent. The transformed target volumes retain different characteristics with respect to shape and/or position. Following registration and transformation, however, the data sets and hence the target volumes may be compared directly with each other. Therefore, the registration at least partially receives the differences between the data sets resulting from a different patient anatomy.

An amalgamation of the target volumes in the data sets is formed with different positions and/or shapes (e.g., using the registrations of the other data sets to the selected data set).

In the selected data set, a risk area that is to be, for example, protected during irradiation is also determined. This may be, for example, one or more organs at risk or, more generally, one or more volumes of critical structures.

The amalgamation of the target volumes is modified in that the area at risk is taken out of (e.g., removed) from the amalgamation of the target volumes.

This modified amalgamation of the target volumes is used when calculating the irradiation treatment plan. The modified amalgamation of the target volumes may identify the volume that is to be irradiated with a desired dose.

The data sets (e.g., imaging data sets of a patient) such as computed tomography scans depict the target volume to be irradiated and may depict one or more volumes of critical structures (e.g., organs at risk (OAR)).

The target volume or volumes and the volume or volumes of critical structures may already be identified or already outlined in the data sets. This may, for example, take place in that the data sets are segmented with the aid of an automatic or semiautomatic segmentation method. However, the identification may also be performed entirely manually. The identification provides that there is an assignment of specific areas of the data set to the target volume and/or to a critical structure and that specific areas of the data set are marked as a target volume and/or as a volume of a critical structure.

With this method, the irradiation treatment plan calculated in this way takes into account any possible changes to the location or position of the target volume (e.g., in that it takes into account a plurality of data sets and actual positional changes of the target volume that occur in reality and forms an amalgamation of different target volume positions or shapes), but takes into account the specific position of the critical structures (e.g., in that the critical structure is only removed from the data set selected as the starting point of the method). Despite the expansion of the target volume, no critical structures that are present on a specific day are targeted. Only what is necessary is removed from the amalgamation of the target volumes.

The method may be repeated several times. On each repetition, another data set is selected as the selected data set from the plurality of data sets. A different irradiation treatment plan is obtained on each repetition. Each of these irradiation treatment plans is assigned to the data set that was selected as the selected data set at the start of the method. This makes a plurality of irradiation treatment plans available. Each treatment plan of the plurality of treatment plans specifically takes into account the location of areas at risk.

The data sets may be recorded on different days. This increases the probability of the individual data sets also containing a different patient anatomy and hence of possible changes in location being taken into account adequately.

For example, one or more of the data sets may be a verification data set that is used when positioning a patient with the target volume in an irradiation chamber. The verification data set may, for example, be recorded on the day of treatment before a treatment session. The verification data set may be used to position the patient appropriately so that the target volume is present at a location, in which matched irradiation is possible. The decision as to whether the patient is actually irradiated in this position is left up to the user (e.g., a doctor), who will decide in each individual case whether the irradiation will actually be performed or whether the irradiation, for example, should not be performed due to the physical condition of the patient.

This method has the advantage that verification data sets, which may be recorded anyway for the positioning of the patient, may simultaneously also be used to compile irradiation treatment plans according to the method described above.

A further development results in a method for the determination of an irradiation treatment plan for a target volume to be irradiated.

In one act, a method as described above is performed so that the data sets of the plurality of data sets are each assigned an irradiation treatment plan. Each data set is assigned the irradiation treatment plan that was compiled with a modified amalgamation of target volumes, in which an area at risk was removed from amalgamation of the target volumes (e.g., with a specific position or location as shown in the respective data set).

In a second act, following the first act, the following acts are performed. A verification data set is recorded, and the verification data set is compared with the data sets, to which irradiation treatment plans are assigned for the determination of the data set with the greatest similarity to the verification data set. The irradiation treatment plan assigned to the data set with the greatest similarity to the verification data set is selected.

The irradiation treatment plan selected for a possible irradiation may best approximate the current patient anatomy. The selected irradiation treatment plan may be communicated to the irradiation device and, for example, loaded into a memory of the irradiation device so that, if a doctor consents to the irradiation, the irradiation may be applied by the irradiation treatment plan.

In one embodiment, an area in the data sets is determined for the comparison of the verification data set with the data sets. The comparison is only performed in the determined area. Only relevant image areas are used for the evaluation of the patient anatomy for the comparison. This enables differences in areas, which, for example, lie a long way from the target volume to be irradiated and therefore do not have any significant influence on relevance when selecting the appropriate irradiation treatment plans, to be excluded during the comparison.

For example, the area may only partially include an organ adjacent to the target volume (e.g., only a side of the organs facing the target volume and therefore lying in an "interface" area for the target volume).

Specific regions may be excluded from the area, in which the comparison of the data sets takes place. For example, regions characterized by air inclusions may not be included in the area and may be selectively excluded. The same applies to regions characterized by specific, predefined tissue types such as, for example, bone tissue.

This all restricts the area for the comparison to regions that have been found to be particularly relevant for the selection of a suitable irradiation treatment plan.

The device for irradiation treatment planning for a target volume to be irradiated includes a computer unit that is, for example, by the embodiment of suitable modules, embodied or configured to load a plurality of data sets. The target volume to be irradiated is depicted in each data set of the plurality of data sets. The data sets differ in that the target volume has another position and/or shape. The computer unit is also configured for the selection of a data set from the plurality of the data sets, for the registration of the other data sets to the selected data set, and for the formation of an amalgamation of the target volumes using the registrations of the other data sets to the selected data set. The computer unit is configured for the determination of an area at risk in the selected data set, for the modification of the amalgamation of the target volumes in that the area at risk is excluded from the amalgamation of the target volumes, and for the calculation of an irradiation treatment plan using the modified target volume.

The computer unit of the irradiation planning device may be embodied or configured to carry out a method, as described above.

The computer unit may also be embodied or configured for the comparison of a verification data set with the data sets of the plurality of the data sets. For example, the computer unit may be embodied or configured for the determination of an area for the comparison of the verification data set with the data sets of the plurality of the data sets and for the performance of the comparison in only the determined area.

The preceding and following description of the individual features and the advantages and impacts thereof refers both to the device and the method without this being explicitly mentioned in each individual case. The individual features disclosed may also be provided in combinations other than those shown.

DETAILED DESCRIPTION OF THE DRAWINGS

Figure 1:
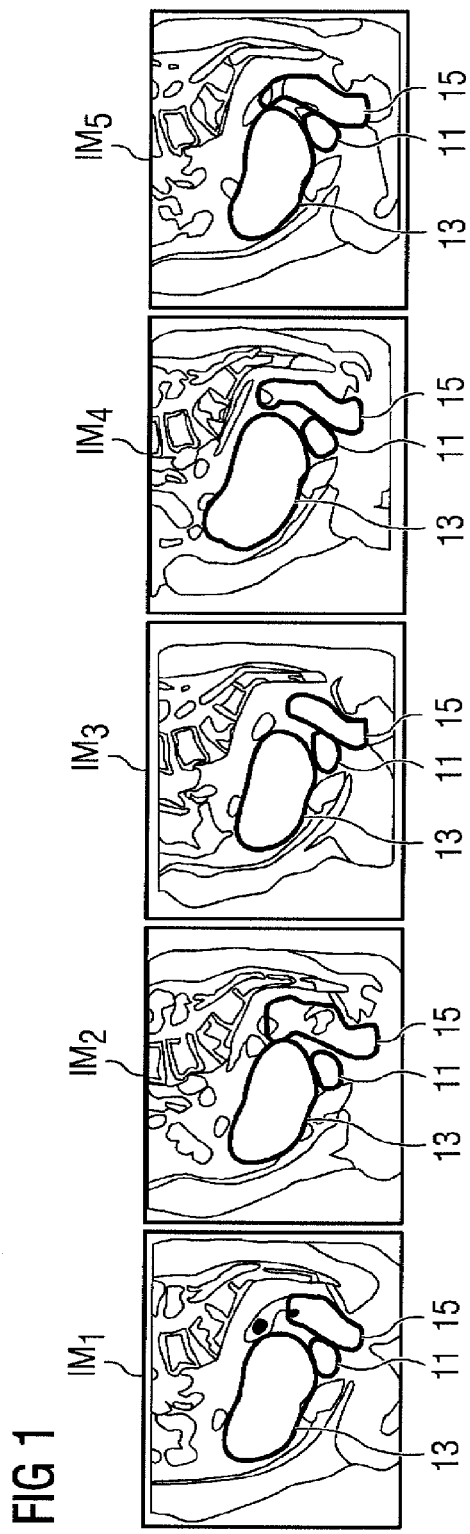
FIG. 1 shows five different exemplary imaging data sets, each of which shows the prostate, the bladder and the rectum of a patient.

FIG. 1 shows the starting point of a method for irradiation treatment planning (e.g., a plurality (five) of different data sets depicting the same anatomy to be irradiated). Since the data sets are produced at different time points, the anatomy of the patient changes slightly. The different data sets (e.g., n data sets) are designated IM1, IM2, . . . to IMn (e.g., IM5).

FIG. 1 shows respective data sets IM1 . . . IM5, in which the target volume to be irradiated (e.g., the prostate 11 of the patient) and organs at risk to be protected (e.g., the bladder 13 and the adjacent rectum 15 of the patient) are segmented and drawn correspondingly. Due to the different filling levels of the bladder 13 and of the rectum 15, a position and a shape of the target volume and the volumes of the critical structures differ slightly from data set to data set.

Figure 2:
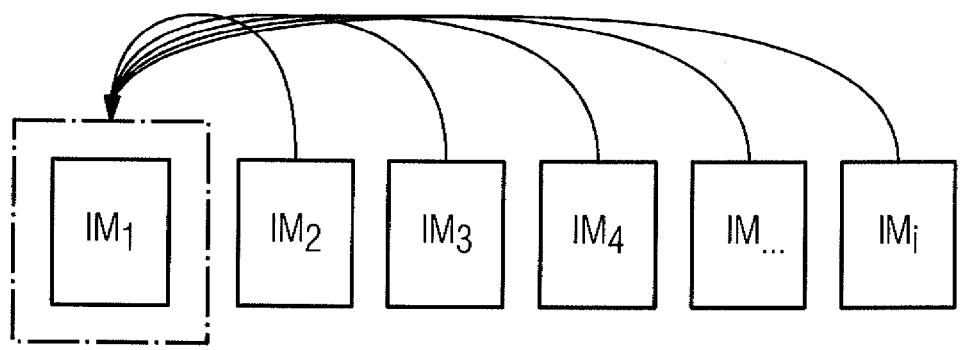
FIG. 2 is a schematic representation of the selection of a data set and the registration of other data sets to the selected data set.

In a first act, all data sets apart from the first data set (e.g., IM2 . . . IMn) are registered to the first data set IM1, as shown in FIG. 2.

The registrations are used to make the data sets comparable with each other. Although the registrations adapt the data sets to each other with respect to translation, rotation and scaling so that the data sets are made directly comparable with each other, the registrations at least partially obtain the specific location and positional differences of the target volume and of the volume or volumes of the critical structures that are caused by the different patient anatomy at the time of the recording of the data sets. The registrations are used to transform the outlined target volumes 11 of the other data sets correspondingly to the first data set.

Figure 3:
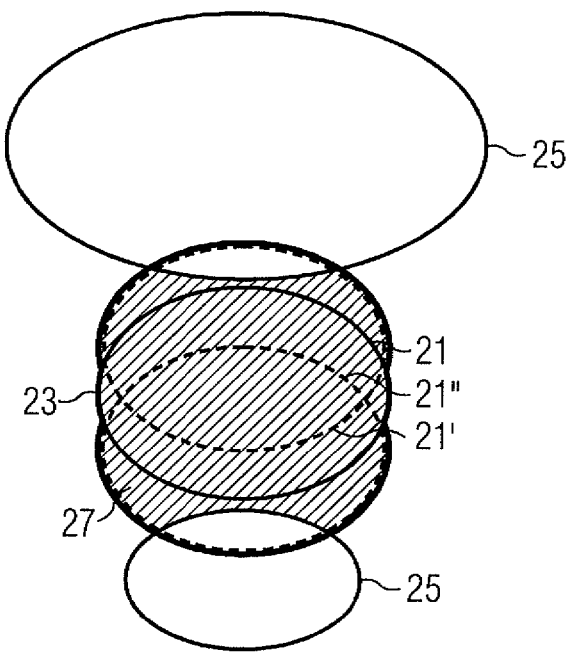
FIG. 3 is a schematic representation of an imaging data set, in which a target volume is shown, positions of two organs at risk, and the corresponding location of target volumes from other imaging data sets.

FIG. 3 shows the method with the possibly transformed target volumes. All the target volumes (e.g., the target volume 21 of the first data set IM1 and the target volumes 21, 21" of the further data sets IM2 . . . IMn) transformed to the first data set are amalgamated. The result is the formation of an amalgamation target volume 23.

The volume or volumes 25 of the critical structures such as those present in the first data set IM1 are removed from this amalgamation target volume 23. This results in a first global target volume, hereinafter designated (GP-OAR)1 (e.g., grey background area 27).

This method is performed for indices i=1 . . . n. This provides that with the i-th index, the data sets IM1 . . . IMi−1, IMi+1, IMn are registered to the i-th data set IMi. The target volumes in the data sets IM1 . . . IMi−1, IMi+1, IMn are transformed on the basis of the registrations to the i-th data set IMi. An amalgamation target volume is formed from the IMi target volume and the transformed target volumes, and the volume or volumes of the critical structures as present in the i-th data set IMi are removed from the amalgamation target volume, so that an i-th global target volume is obtained (e.g., designated (GP-OAR)i).

An irradiation treatment plan TPi is compiled for each index i=1 . . . n. This irradiation treatment planning uses the data set IMi and the i-th global target volume (GP-OAR)i determined according to the above method and may, based on these specifications, be performed according to a conventional irradiation treatment planning method.

For example, in one embodiment, the volume or volumes of the structures to be protected that are present in the data set IMi may be taken into account such that for the volumes, boundary conditions to be adhered to are specified (e.g., a maximum dose to be applied or a dose-volume boundary condition).

The plurality of irradiation treatment plans TPi, i=1 . . . n is stored in an irradiation treatment plan database. Each irradiation treatment plan TPi is assigned to the initial data set IMi, to which the other data sets are registered.

This may take place in a first act (e.g., prior to a planned irradiation session).

Before the irradiation session is commenced, an additional data set IMd depicting the current position of the target volume and hence the current patient geometry (hereinafter designated a verification data set) is recorded. The verification data set may, for example, be used to position the patient in a treatment chamber or for a planned treatment. This enables the target volume to be positioned at a suitable place so that the target volume may be irradiated as planned.

The verification data set IMd is used to select the suitable irradiation treatment plan from the plurality of irradiation treatment plans TPi. To do this, a comparison of the verification data set IMd with the data sets IMi is performed in order to determine a measure of similarity that indicates how similar the verification data set IMd is to the data sets IMi. Different known procedures such as, for example, the sum of the squared differences, correlation coefficient or mutual information may be used in order to quantify the similarity with a measure.

In one embodiment, the similarity is not compared for the entire image information in the data sets but only in a specific image area, a specific sub-volume (e.g., a mask).

Figure 4:
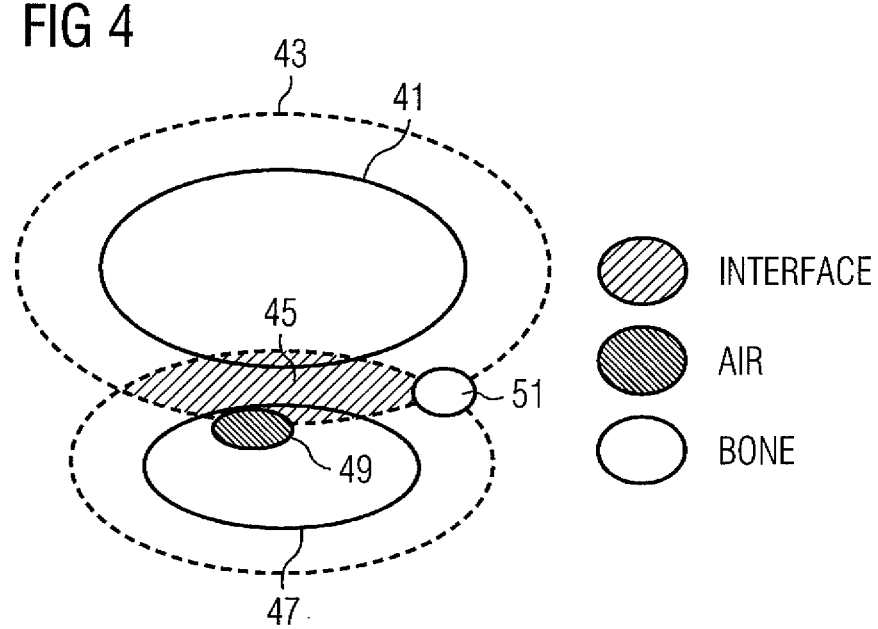
FIG. 4 is a schematic representation of an exemplary mask used for the comparison of similarity with two data sets.

The following discloses how a mask may be determined in this way with reference to FIG. 4.

The mask may be determined as follows: in the data set IMi, the target volume 41 is initially expanded with the aid of a box to produce an expanded target volume 43.

The data set may, for example, be a computed tomography data set (CT data set) with a slice thickness of 3 mm (z direction) and a pixel size of 2×2 mm (x or y direction), for example. With a box size of 3×3×2 voxels (in the x, y, z directions), a geometric box size of 6 mm×6 mm×6 mm is obtained. If the CT data set has a different resolution, the size of the expansion box may be adjusted correspondingly in order to achieve a desired geometric size of the expansion box.

The expanded target volume is expanded with interfaces 45 to adjacent organs 47 to be protected (also designated OAR for "organs at risk"). If the target volume is a prostate, the interfaces to the bladder and to the rectum may be selected.

The interfaces may be determined in that the overlapping voxels between the target volume 41 and the OAR 47 are taken and expanded to an expanded interface region.

For example, with the aforementioned CT data set example for the expansion of the interfaces, an expansion box with a size of 5×5×3 voxels (in the x, y, z directions), for example, may be taken. During the expansion of the interfaces, voxels that contain air 49 or may be assigned to a specific, predefined tissue such as, for example, bone 51 may be excluded.

The mask may be formed such that the expanded target volume is amalgamated with the expanded interface region.

The mask identifies the area of the i-th data set IMi, which is used for the comparison with the current verification data set and is evaluated with respect to the similarity.

The irradiation treatment plan TPi that is assigned to data set IMi that has the highest mutual information, the highest correlation coefficients and/or the lowest sum of squared differences when compared with the verification data set IMd may be selected.

The irradiation treatment plan TPi may be exported and/or loaded into an irradiation system. This makes the irradiation treatment plan available for any subsequent irradiation performed.

Figure 5:
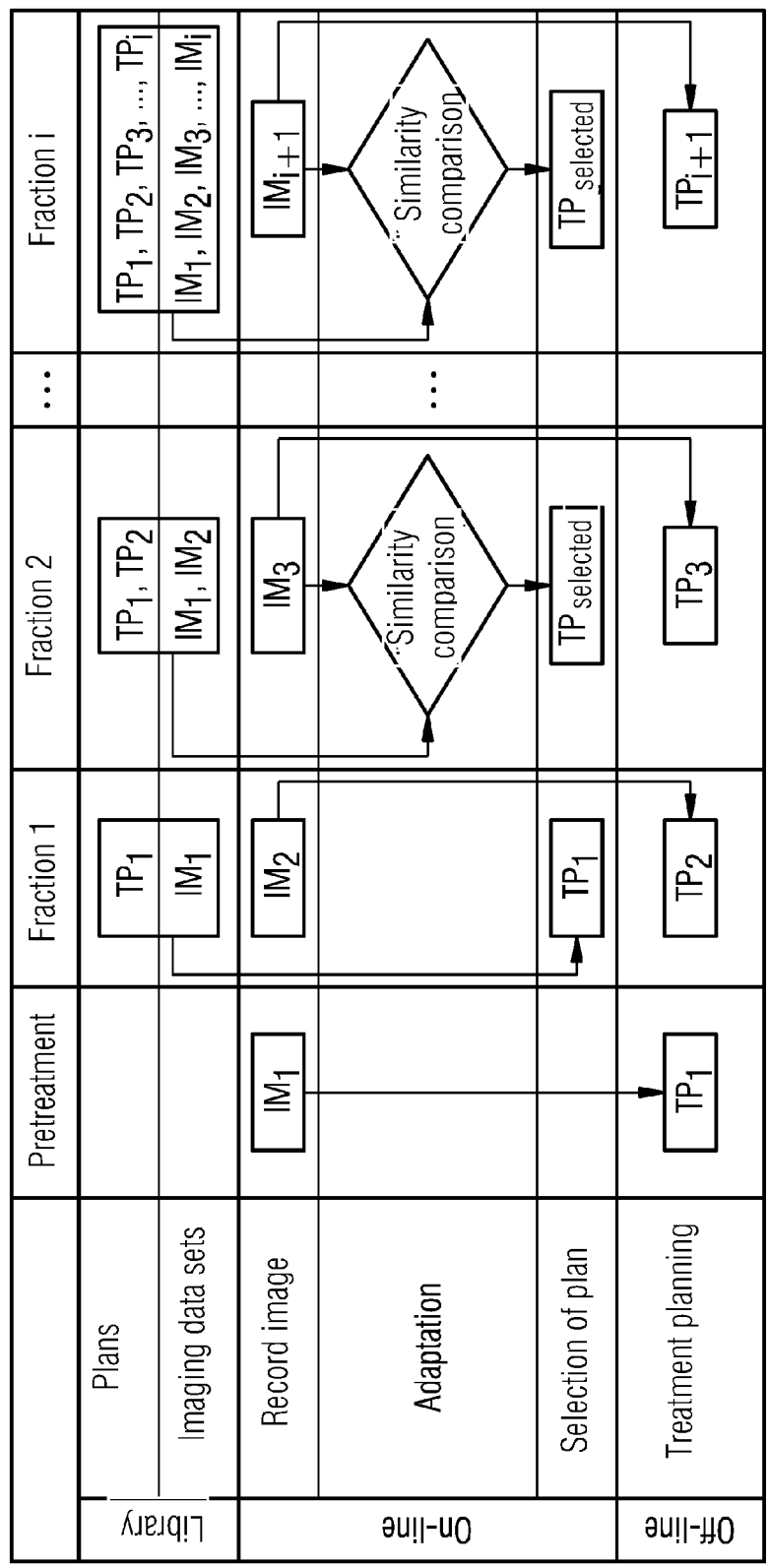
FIG. 5 is a flow diagram of one embodiment of a method for irradiation treatment planning.

In clinical practice, it is not usual to record a plurality of CT data sets prior to irradiation in order to calculate a plurality of irradiation treatment plans therefrom. However, the above-described method may be implemented such that a database with possible irradiation treatment plans TPi is expanded successively. An exemplary flow diagram is explained with reference to FIG. 5.

Prior to a planned irradiation, a first CT data set IM1 is compiled, and the planning is based on the first CT data set IM1 (the left column "Before treatment"). As a result, a first irradiation treatment plan TP1 is compiled.

During a first irradiation session (the column "Fraction 1"), the first irradiation treatment plan TP1 may be selected and loaded into the irradiation system. If the doctor or user gives consent, the first irradiation treatment plan TP1 may be applied.

During the first irradiation session, a further CT data set IM2 is compiled for use during the first irradiation session for the positioning of the patient or for position verification.

Following the first irradiation session, there are two data sets available, IM1 and IM2. The method described with reference to FIG. 1 to FIG. 4 may be applied "offline" in order to determine a second irradiation treatment TP2 plan from IM2 with the incorporation of IM1.

Two irradiation treatment plans TP1 and TP2 are available for the second irradiation session (the column "Fraction 2"). A verification data set IM3 recorded for the positioning of the patient for the second irradiation session may be used for the position verification.

This verification data set IM3 may be compared with the data sets IM1 and IM2 in order to use the above-described method for the determination of the measure of similarity to determine the most suitable irradiation treatment plan from the two irradiation treatment plans TP1 and TP2 available.

With further fractions, the method may be further performed in a similar way (e.g. the column "Fraction i"). For an i-th irradiation session, a verification data set IMi+1 is recorded. The recorded verification data set IMi+1 is compared with the existing data sets IM1 . . . IMi in order to select the best of the irradiation treatment plans TP1 . . . TN already compiled. Offline, the verification data set IMi+1 may be used as data set IMi+1 in order to expand the library of the available irradiation treatment plans TP1 . . . TPi by a further irradiation treatment plan TPi+1.

Figure 6:
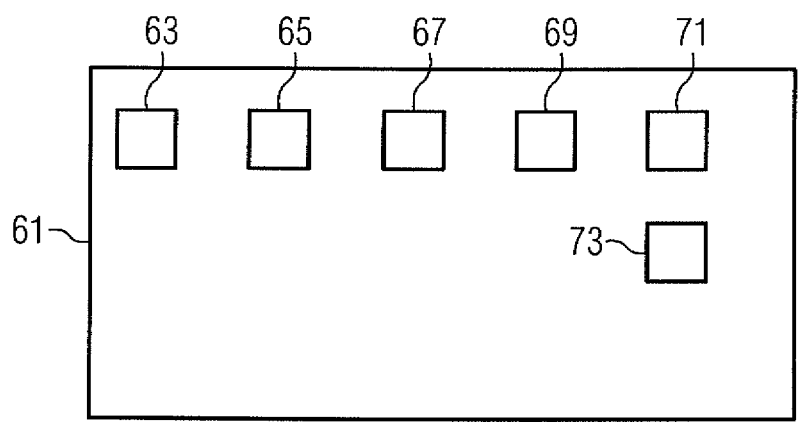
FIG. 6 shows one embodiment of an irradiation planning device.

FIG. 6 shows the components of one embodiment of an irradiation planning device, with which the above-described method may be performed. The device and the components thereof may be implemented, for example, in a computer system 61.

The device for irradiation treatment planning includes an interface 63, via which the data sets may be loaded. A plurality of data sets, in each of which the target volume to be irradiated is depicted, may be loaded. The data sets differ in that the target volume has another position and/or shape.

The device includes a selection device 65 that is configured such that one data set is selected from a plurality of data sets.

The device includes a registration device 67 that is configured such that, on the basis of the selection of the selection device, other data sets are registered to the selected data set.

The device also includes a target volume determination device 69 that is configured such that an amalgamation of the target volumes is formed using the registrations of the other data sets to the selected data set. The target volume determination device is also configured for the modification of the amalgamation of the target volumes in that the area at risk is excluded from the amalgamation of the target volumes.

The device includes a planning device 71 that is configured, using the modified target volume amalgamation based on the target specifications, to carry out irradiation treatment planning.

The device also includes a comparison device 73 that is configured for the comparison of a verification data set with the data sets of the plurality of the data sets.

The comparison device is, for example, configured such that an area for the comparison of the verification data set with the data sets of the plurality of the data sets is determined, and the comparison is only performed in this area.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for irradiation treatment planning for a target volume to be irradiated, the method comprising:
    specifying, using a computer, a plurality of data sets having at least three data sets, the target volume to be irradiated being depicted in each data set of the plurality of data sets, wherein the target volume to be irradiated has a different position, shape, or position and shape in each data set of the plurality of data sets;
    selecting, using the computer, a data set from the plurality of the data sets;
    registering, using the computer, other data sets of the plurality of the data sets to the selected data set;
    forming, using the computer, an amalgamation target volume of the depicted target volumes by combining the target volumes in the registered data sets and the selected data set into a single volume;
    determining, using the computer, an area at risk in the selected data set;
    modifying, using the computer, the amalgamation target volume such that the area at risk is excluded from the amalgamation target volume; and
    calculating, using the computer, an irradiation treatment plan using the modified amalgamation target volume.

2. The method as claimed in claim 1, further comprising calculating a separate irradiation treatment plan for each of the other data sets in the plurality of data sets through a repetition of the selecting, the registering, the forming, the determining, the modifying, and the calculating, thereby forming a plurality of irradiation treatment plans.

3. The method as claimed in claim 1, wherein the plurality of data sets is recorded on different days.

4. The method as claimed in claim 1, wherein at least one data set of the plurality of data sets is a verification data set that is used for planned treatment during the positioning of a patient with the target volume to be irradiated.

5. The method as claimed in claim 2, wherein the plurality of data sets is recorded on different days.

6. The method as claimed in claim 2, wherein at least one data set of the plurality of data sets is a verification data set that is used for planned treatment during the positioning of a patient with the target volume to be irradiated.

7. The method as claimed in claim 3, wherein at least one data set of the plurality of data sets is a verification data set that is used for planned treatment during the positioning of a patient with the target volume to be irradiated.

8. A method for the determination of an irradiation treatment plan for a target volume to be irradiated, the method comprising:
    executing a method for irradiation treatment planning, for the target volume to be irradiated so that each data set of a plurality of data sets having at least three data sets is assigned one irradiation treatment plan of a plurality of irradiation treatment plans, the method for irradiation treatment planning comprising:

specifying the plurality of data sets, the target volume to be irradiated being depicted in each data set of the plurality of data sets, wherein the target volume to be irradiated has a different position, shape, or position and shape in each data set of the plurality of data sets;

selecting, using a computer, a data set from the plurality of the data sets;

registering, using the computer, other data sets of the plurality of the data sets to the selected data set;

forming, using the computer, an amalgamation target volume of the depicted target volumes by combining the target volumes in the registered data sets and the selected data set into a single volume;

determining, using the computer, an area at risk in the selected data set;

modifying, using the computer, the amalgamation target volume such that the area at risk is excluded from the amalgamation target volume; and calculating, using the computer, an irradiation treatment plan using the modified amalgamation target volume;

computing, using the computer, a separate irradiation treatment plan for each of the other data sets in the plurality of data sets through a repetition of the selecting, the registering, the forming, the determining, the modifying, and the calculating, thereby forming the plurality of irradiation treatment plans;

recording a verification data set;

comparing the verification data set with the plurality of data sets, to which the plurality of irradiation treatment plans is assigned, for the determination of a data set of the plurality of data sets with the greatest similarity to the verification data set; and selecting the irradiation treatment plan assigned to the data set of the plurality of data sets with the greatest similarity to the verification data set.

9. The method as claimed in claim 8, wherein the comparing comprises determining an area in the plurality of data sets, and the comparison is only performed in the determined area.

10. The method as claimed in claim 9, wherein the determined area includes only a part of an organ adjacent to the target volume to be irradiated.

11. The method as claimed in claim 9, wherein the determined area does not include a region characterized by air or by bone tissue.

12. The method as claimed in claim 10, wherein the determined area does not include a region characterized by air or by bone tissue.

13. A device for irradiation treatment planning for a target volume to be irradiated, the device comprising:

a computer system configured to:

load a plurality of data sets having at least three data sets, the target volume to be irradiated being depicted in each data set of the plurality of data sets, wherein the target volume to be irradiated has a different position, shape, or position and shape in each data set of the plurality of data sets;

select a data set from the plurality of the data sets;

register other data sets of the plurality of data sets to the selected data set;

form an amalgamation target volume of the depicted target volumes by combining the target volumes in the registered data sets and the selected data set into a single volume;

determine an area at risk in the selected data set;

modify the amalgamation target volume such that the area at risk is excluded from the amalgamation target volume; and calculate an irradiation treatment plan using the modified amalgamation target volume.

14. The device as claimed in claim 13, wherein the computer system is configured to calculate a separate irradiation treatment plan for each of the other data sets of the plurality of data sets in that the computer system is configured to repeatedly select, register, form, determine, modify, and calculate for the each of the other data sets of the plurality of data sets.

15. The device as claimed in claim 13, wherein the computer system is configured to compare a verification data set with data sets of the plurality of the data sets.

16. The device as claimed in claim 14, wherein the computer system is configured to compare a verification data set with data sets of the plurality of the data sets.

17. The device as claimed in claim 15, wherein the computer system is configured to:

determine an area for the comparison of the verification data set with the data sets of the plurality of the data sets; and perform the comparison in only the determined area.

18. The device as claimed in claim 17, wherein the computer system is configured to determine the area such that the area includes only a part of an organ adjacent to the target volume to be irradiated.

19. The device as claimed in claim 17, wherein the determined area does not include a region characterized by air or by bone tissue.

20. The device as claimed in claim 18, wherein the determined area does not include a region characterized by air or by bone tissue.

* * * * *